United States Patent
Murata et al.

(10) Patent No.: US 8,647,263 B2
(45) Date of Patent: Feb. 11, 2014

(54) ILLUMINATION OPTICAL SYSTEM FOR ENDOSCOPES

(75) Inventors: Keiji Murata, Shibuya-Ku (JP); Hiroshi Tsuyuki, Shibuya-Ku (JP); Daisuke Akiyama, Shibuya-Ku (JP)

(73) Assignee: Olympus Medical Systems Corp., Tokyo (JP)

( * ) Notice: Subject to any disclaimer, the term of this patent is extended or adjusted under 35 U.S.C. 154(b) by 1300 days.

(21) Appl. No.: 12/465,088

(22) Filed: May 13, 2009

(65) Prior Publication Data

US 2009/0287057 A1    Nov. 19, 2009

(30) Foreign Application Priority Data

May 14, 2008 (JP) .................................. 2008-126911

(51) Int. Cl.
*A61B 1/00* (2006.01)
*A61B 1/04* (2006.01)

(52) U.S. Cl.
USPC ........... 600/177; 600/160; 600/161; 359/385; 359/664; 362/574; 362/336

(58) Field of Classification Search
USPC .................. 600/160, 161, 177; 359/385, 664; 362/574, 336
See application file for complete search history.

(56) References Cited

U.S. PATENT DOCUMENTS

| | | | | |
|---|---|---|---|---|
| 4,580,552 A * | 4/1986 | Nishioka et al. | ............... | 600/177 |
| 5,047,847 A * | 9/1991 | Toda et al. | ........................ | 348/68 |
| 5,188,092 A * | 2/1993 | White | ........................... | 600/167 |
| 5,354,322 A * | 10/1994 | Miyano | ........................... | 607/88 |
| 5,403,308 A * | 4/1995 | Wood et al. | ........................ | 606/17 |
| 6,206,825 B1 * | 3/2001 | Tsuyuki | ........................ | 600/182 |
| 6,252,722 B1 * | 6/2001 | Kittaka et al. | ................ | 359/654 |
| 6,263,133 B1 * | 7/2001 | Hamm | ............................ | 385/33 |
| 2001/0003142 A1 * | 6/2001 | Koshikawa | ................... | 600/177 |
| 2001/0055462 A1 * | 12/2001 | Seibel | ............................ | 385/147 |
| 2003/0233138 A1 * | 12/2003 | Spooner | ........................ | 607/93 |
| 2004/0073120 A1 * | 4/2004 | Motz et al. | ..................... | 600/478 |
| 2006/0171025 A1 * | 8/2006 | Quake et al. | ................... | 359/368 |

* cited by examiner

*Primary Examiner* — John P Leubecker
*Assistant Examiner* — Arnaldo Torres Diaz
(74) *Attorney, Agent, or Firm* — Arnold International; Bruce Y. Arnold

(57) ABSTRACT

The invention provides lenses at low cost, which form an illumination optical system for endoscopes that has high efficiency and achieves improved light distribution. The illumination optical system for endoscopes is used in opposition to a light beam exit end 1 of a transmission means F for light emitted from a light source, and comprises, as viewed from the light beam exit end 1, a lens group 10 having positive power and an optical member 20 subsequent thereto which has a spherical surface 20a that functions as a lens, has a radius of curvature R, and satisfies the following condition:

$$1.48 \leq S/\pi R^2 \leq 4 \qquad (1)$$

where
R is the radius of curvature of the spherical surface, in mm, and
S is a surface area of the spherical surface, in mm$^2$.

14 Claims, 6 Drawing Sheets

Example 7

Example 8

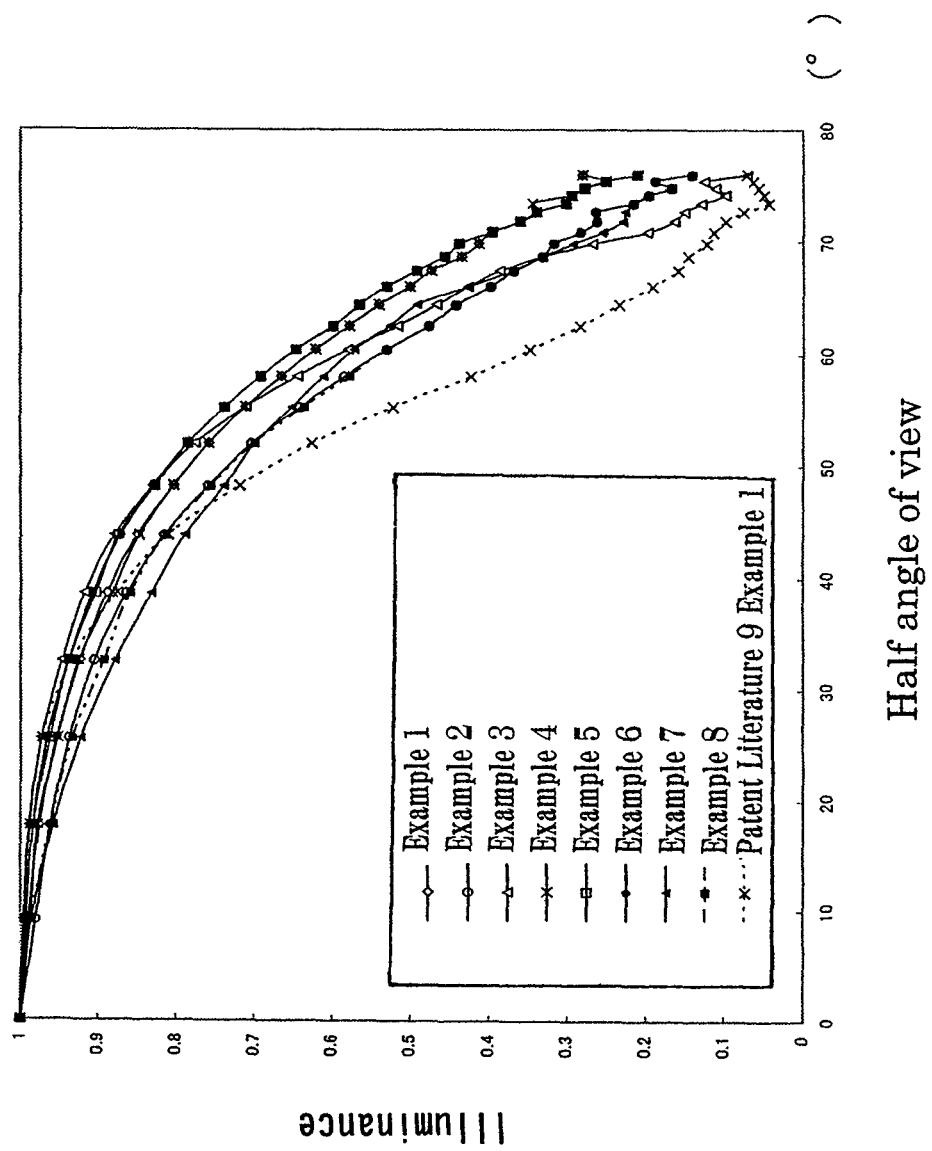

ILLUMINATION OPTICAL SYSTEM FOR ENDOSCOPES

BACKGROUND OF THE INVENTION

The present invention relates generally to an illumination optical system for endoscopes, and more particularly to an illumination optical system for endoscopes that is used in opposition to a light beam exit end of a light transmission means for transmission of light from a light source and that is designed especially for a slimmed-down endoscope.

For a scope used for endoscopic inspection, there has been mounting demand toward a wide-angle field of view in view of prevention of making an oversight. In recent years, some scopes having a full angle of view from 140° to 170° have been available. To obtain wide-angle subject images, it is indispensable to make the angle of field of an objective lens wider; however, if the ability of an illumination optical system to distribute light to the periphery of the field of view is worse, an effective viewing angle then becomes narrow too. Accordingly, when it comes to making the field of view of an endoscope wider, the ability of the illumination optical system to distribute light over a wider range must be factored in.

On the other hand, much is still left to be desired about the diameter of the scope itself for the purpose of easing off pains to patients. The requirements for such an illumination optical system as used on endoscopes are that the distribution of light to around the field of view be satisfactory and, moreover, the diameter of an illumination lens be small. The situations being like this, for an illumination optical system adapted to diverge rays just emitted from a light beam exit end via a negative lens as shown typically in Patent Publication 1, it is required to make the diameter large, thereby preventing the ability to distribute light from going worse by shading. As a result, the proportion of the area of the illumination lens in the scope's leading end grows high, rendering diameter reductions difficult. As shown in Patent Publications 2 and 3, there are some attempts at improving the ability to distribute light using a less costly member such as an inexpensive-to-fabricate transparent sphere. Nonetheless, there are still similar problems remaining unsolved because they take aim at wide light distribution by divergence using a negative lens as is the case with Patent Publication 1.

The situations being like such, most illumination optical systems for endoscopes make use of positive lenses, as exemplified in Patent Publications 4 to 9. Once a light beam has been collected in the illumination optical system, it is turned into divergent light for illumination. By doing this, diameter reductions are achievable while the ability to distribute light is improved, thereby making the diameter of the scope small.

And now, it is general that subjects viewed mainly through endoscopes are not always of constant shape. There are many subjects such as the wall of the abdominal cavity that is relatively close to a plane, the internal wall of the digestive tract in a tract and cavity form, the cardiac region or its vicinity that is close to spherical shape, or the like.

For instance, when a planar subject is viewed, it is well known as the cosine forth law that as an aberration-free optical system having limited quantity losses is used, it causes a relative illuminance distribution to decrease in proportion to $\cos^4\theta$. Accordingly, the use of this for illumination would cause the periphery to get dark: this is the reason the aberration-free lens (f·tan θ lens) is not suited for illumination. To obtain uniform illuminance over the field of view in the case of a planar subject, it is preferable to use a regular projecting lens (f·sin θ lens), as set forth in detail in Patent Publication 4.

When a curved subject such as a spherically shaped subject is viewed, on the other hand, it is preferable to use an equidistant projecting lens (fθ lens) that satisfies h=fθ where h is the height of light incident onto the illumination optical system, θ is an exit angle, and f is the focal length of the illumination optical system. With this, it is possible to obtain uniform illuminance on the spherical surface and so obtain an image that is easiest to view, as set forth in detail in Patent Publication 5.

What is common to these is that to improve light distribution capability using the illumination optical system, large distortion must be produced.

Of course, if an aspheric surface is used as shown in Patent Publications 4, 5 and 6, it is then possible to produce large distortion, thereby achieving wide light distribution. However, the angle of field of the objective lens grows wide, and if it is intended to obtain wide light distribution over a wider range, it is then required to configure the lens into a steeper convex shape. As a result, power grows strong and so high precision is in demand. This leads to a problem: cost rises. The aspheric surface is processed mainly by molding at the cost of the degree of freedom in selection of materials, because the glass material capable of molding is limited. In other words, fine adjustment cannot be implemented by material replacement.

In addition, the above theory should be applied to where there is none of losses caused by shading of rays in an optical path: the fact that the above illumination optical system is idealized too far must be taken into account. That is, especially with an endoscope illuminating optical system that places weight on fineness, care should also be taken of how light quantity can be delivered with no quantity losses. In other words, light rays are indeed shaded by a frame or the edge of the lens en route to the periphery of the field of view: it is difficult to deliver light rays up to the periphery of the field of view. For instance, referring to such an optical system as shown in Patent Publications 7, 8 and 9, the applicable angle of field is barely about 120° at most; in other words, with a scope of 140° or greater, it is difficult to improve light distribution.

There are two reasons: (A) distortion produced at the illumination optical system remains small so that light is likely to be collected at the center, making light quantity at the periphery smaller than that at the center; and (B) when it is intended to produce large distortion, light leaving parallel with an optical path is likely to be shaded on the way to the periphery of the field of view, resulting in efficiency losses of the illumination system. For two such reasons, there can be no tradeoff offered between efficiency and light distribution. In addition, as the diameter of the scope gets smaller, influences of decentration, if not large, grow larger. For instance, there is a phenomenon where illumination light is locally biased. Accordingly, strict tolerance must be applied to parts, and processing costs rise as well.

Patent Publication 1: JP(A) 2003-131144
Patent Publication 2: JU(A) 5-94835
Patent Publication 3: JP(A) 2005-304838
Patent Publication 4: JP(A) 2003-5095
Patent Publication 5: JP(A) 5-157967
Patent Publication 6: JP(A) 6-148519
Patent Publication 7: JP(A) 8-320440
Patent Publication 8: JP(A) 2000-275547
Patent Publication 9: JP(A) 2002-182126

SUMMARY OF THE INVENTION

Having been made with such problems with the prior art in mind, the present invention has for its object to provide at low costs lenses for an illumination optical system for endoscopes, which has high efficiency and is well capable of distributing light.

According to the invention, the above object is accomplishable by the provision of an illumination optical system for endoscopes, which is used in opposition to a light beam exit end of a transmission means for light emitted from a light source, characterized by comprising, as viewed from said light beam exit end, a lens group having positive power and an optical member subsequent to thereto which has a spherical surface that functions as a lens, has a radius of curvature R, and satisfies the following condition:

$$1.48 \leq S/\pi R^2 \leq 4 \tag{1}$$

where

R is the radius of curvature of the spherical surface, in mm, and

S is the surface area, in mm², of the spherical surface.

Reference is now made to the requirements for, and the advantages of, the above arrangement of the inventive illumination optical system for endoscopes.

For the illumination optical system comprising a positive lens group, there must be a sensible tradeoff between high efficiency and wide light distribution. To this end it is required to get rid of shading in an optical path and deliver light biased to the center of the field of view in a conventional optical system over to the periphery of the field of view. Ordinarily, light rays out of the light beam exit end of the light transmission means have some angular distribution. To address the above two problems separately, however, a light beam leaving the light beam exit end parallel with an optical axis (hereinafter called the parallel light beam) and a light beam leaving the light beam exit end at an angle with the optical axis (hereinafter called the oblique light beam) are considered separately. The former contributes mainly to illumination efficiency, and the latter mainly to light distribution on the periphery.

If the power of each lens in the illumination optical system is increased for wider light distribution, as shown in FIG. 1, shading is likely to take place of light rays that are contained in the parallel light beam 21 coming out of the light beam exit end 1 of a light transmission means F and incident onto the illumination optical system with a large height h. Especially if the power of an end lens 20 in the illumination optical system is increased, shading is more likely to take place. On the other hand, however, unless a light ray 22 that is in light rays out of the light beam exit end 1 and has an angle with the optical axis is largely bent and carried up to the periphery of the field of view, there is no improvement in light distribution. In other words, there must be large distortion and access to much light: there is no option but to diminish the radius of curvature of the end lens 20 in the illumination optical system.

According to the invention, as shown in FIG. 3, an extensive surface 20a having a small radius of curvature and strong power is provided so that the parallel light beam 21 is once collected at substantially the center of curvature of that surface 20a, while the oblique light beam 22 is largely bent and carried up to the periphery of the field of view.

With this arrangement, the parallel light 21 is collected substantially at the center of curvature of the surface 20a so that at a boundary with the refractive surface 20a, incident light and refracted light are going to travel substantially along the normal to the surface. Accordingly, the refraction of light at this portion is so minimized that shading of light rays caused by a sudden refraction of light through the end lens 20 is reduced. In addition, this takes effect irrespective of refractive index and, compared with the use of a molded lens, makes sure there is freedom in selecting the glass for the end lens 20 in order to adjust light distribution.

Generally, the end surface of an optical system used for the leading end of an endoscope has a planar shape for the purpose of improving insertion capabilities and keeping cleanness. To obtain a measure of how the oblique light beam spreads out, an argument here is based on the premise that light refracted through a refractive surface having a radius R goes straight, immediately entering and leaving that surface. The oblique light beam 22 is refracted through the lens group 10 of positive power in the illumination optical system, and so enters the end lens 20 at various angles. Here a light ray leaving at the largest angle is incident onto an edge portion of a rear end surface 20a of the end lens 20 and parallel with the optical axis. Let θ be an exit angle of such a ray out of the end surface 20b and n be the refractive index of the end lens 20, and the following equations hold from Snell's law with reference to FIG. 5.

$$\sin \theta = n \cdot \sin \alpha \tag{a}$$

$$n \cdot \sin \beta = \sin \phi \tag{b}$$

Here φ is the angle of incidence of light onto the rear end surface 20a, b is the angle of refraction of light through the rear end surface 20a, and α is the angle of incidence of light onto the end surface 20b. From geometrical considerations, there is $$\phi = \alpha + \beta \tag{c}$$

Solving this with respect to φ and eliminating α and β from the three equations (a), (b) and (c) gives $$\phi = \arctan [\sin \theta / \{(n^2 - \sin^2 \theta)^{1/2} - 1\}] \tag{d}$$

Wide light distribution may be needed for a scope having an angle of field of 140° or greater but, of course, if variations of parts, assembling or the like add, the JIS standards allow for about ±15%. In consideration of the need of spreading out light to about 160° that is the maximum angle of view, the aforesaid oblique light beam needs to be spread out to about θ=80.0°. This is an improvement in light distribution that can be obtained by varying the index of refraction of the optical material. Let θ=80.0° be substituted in into the above equation (d), and let n be equal to 1.6 so as to guarantee the application of this to a low-refractive index optical material. Then Φ=75° is obtained. Namely, if Φ is larger than 75°, it is then possible to achieve wide light distribution in the case of using a vitreous material of n≥1.6. Here, from $$2\pi \text{rad } (x), \text{ and}$$

$$S = \int d\phi \int R^2 \sin\theta \, d\theta$$

the minimum area of such a refractive surface is found to be 1.48πR². Here rad(x) is written as a function with a radian calculated factor x. From this, combined with the fact that the largest possible area is 4πR², the above condition (1) is obtainable.

It is more preferable to narrow condition (1) down to condition (1').

$$2 \leq S/\pi R^2 \leq 4 \tag{1'}$$

The reason is that, if condition (1') is satisfied, at least a half of the sphere with the radius R can be covered with a refractive surface having the radius R so that the outer diameter of the lens is fixed at 2R. Generally, an optical member of strong power must be made with considerable precision, and so processing costs tend to increase. However, the above ball shape can be processed with high precision, because if its curved surface is guaranteed, so would be its outer diameter. It is thus possible to provide lenses of improved precision at lower cost.

For the purpose of achieving further cost reductions, it is preferable to use for the above optical system a sphere that has a radius R and satisfies $S/\pi R^2 = 4$. Only by processing a ball lens, it is thus possible to process both surfaces of the optical member: the surface on the light beam exit end side (the trailing end surface) and the surface facing the object to be illuminated (the leading end surface). In other words, it is possible to obtain lenses that have improved precision yet at lower costs.

Alternatively, when ease of handling is balanced against production costs, use may be made of a double-convex lens both surfaces of which have a radius R and whose centers are in alignment. A spherical lens component is originally devoid of directionality; however, when there is a flaw on the lens or the coating peels off, it should preferably have directionality, because it can easily be handled. If an edge thickness difference is gained by use of the above lens configuration, there is then good stability obtainable. For processing of such a lens, processing into spherical shape plus centering for cutting off the outer diameter is only needed, and cost increases are minimized.

If weight is on light distribution, then a positive lens whose outer diameter is determined by the aforesaid spherical surface having the radius R may be used as the aforesaid optical member. Even if the maximum efficiency is achieved, illumination light unavoidably undergoes quantity losses caused by shading in an optical path, and if the end lens has a long total length, that is likely to occur in the oblique light beam. Accordingly, if the end lens is kept short and the proportion of shading is reduced that much, it is then possible to distribute light up to the periphery of the field of view.

More preferably, such a positive lens should be a plano-convex positive lens, not only because processing into plane is simplest, and but also because if the outer diameter is determined by the spherical surface having the radius R, there is then an optical thickness of greater than R obtainable so that the center of the surface having the radius R can be located in the lens. In the invention, this is almost tantamount to locating the focus of the illumination optical system (the collection point of the parallel light beam) in the lens: there is no risk of thermal injuries whatsoever.

For an endoscope, it is generally known that its leading end is provided with a hard, transparent covering member for the purpose of resistance to chemicals, impacts or the like. Possible materials to this end include glass materials having high Mohs hardness, and crystalline materials such as sapphire. In the invention, too, the location of the transparent covering member could be effective; however, it is then desired that the material have the same sign as that of the radius of curvature of the surface of the above optical member facing the object to be illuminated or an infinite radius of curvature, and the material be in at least partial contact with the above optical member. The above optical member, because of having a small radius of curvature, has the feature of being susceptible of decenteration during assembling, and especially of tilted decentration that causes a tilt of the optical axis. However, such decentration could be held back by bringing another member having a radius of curvature of the same sign in contact and engagement with the optical member.

For removal of surface decentration, it is desired that the above transparent covering member have the same radius of curvature as that of the optical member. This allows both to be in optical contact with each other, and so is advantageous in that quantity losses become small on the surfaces of contact. Of course, given the same curvature, both may be cemented together into one lens.

In addition, there is an occasion where after use, an endoscope is sterilized by hot vapor in an autoclave. In that case, the end lens of the endoscope must be affixed to a frame. According to the above arrangement, the transparent covering member can be affixed to the frame for putting away the illumination lens for accommodation in the autoclave.

Preferably in view of illumination variations, it is preferable that the lens in the lens group of positive refractive power and positioned nearest to the light beam exit end is a rod lens. A problem with the aforesaid illumination system using a convex lens is that an image at the light beam exit end is going to be transferred onto the subject upon imaging. For instance, when the light beam exit end used is opposition to the illumination lens is formed of light guide fibers, there is a hexagonal close-packed lattice variation occurring due to the fact that such fibers do not provide a uniform surface light source. This may be overcome by roughening the lens surface, but illumination efficiency becomes worse due to quantity losses. According to the aforesaid arrangement, such a light beam can be configured by core-and-clad total reflection into a substantially uniform light beam so that uniform light distribution is achievable.

And when it is desired to improve such an illumination optical system for the distribution of light to around the field of view, the above rod lens should preferably be configured as a double-convex lens. This permits light out of the light beam exit end to undergo refraction upon incidence onto the rod lens, so that the proportion of the parallel light beam gets low whereas the proportion of the oblique light beam grows high. This ensures that light contributing to efficiency when the rod lens is configured as a plano-convex lens can be utilized for distributing purposes: it is possible to achieve further improvements in the distribution of light up to the periphery of the field of view.

In a conventional illumination optical system for endoscopes, a lens-to-lens distance is determined by a spacer tube, but some rays are shaded by such a spacer tube, offering one reason for quantity losses. And as the endoscope gets thinner, even a spacer tube of identical thickness is going to account for a larger portion of quantity losses. To overcome this, all lenses in the lens group should preferably be engaged with an adjacent lens in the lens group at their vertexes so that the lenses can be positioned by that engagement and the frame. It is thus possible to minimize shading in the optical path and so enhance efficiency.

Even more preferably, the lens group is designed such that all lenses thereof are engaged with an adjacent lens of the lens group at their vertexes so that they are positioned by that engagement and the frame. From the light beam exit end, the lens group of positive power is followed by the spherical surface that functions as a lens, has a radius R, and satisfies Condition (1), where S is the surface area of the spherical surface. It is thus possible to achieve an illumination optical system that is improved in the ability to distribute light and has greater efficiency.

According to the invention, it is possible to achieve lenses in the illumination optical system for endoscopes, which has high efficiency and are improved in the ability to distribute light.

Still other objects and advantages of the invention will in part be obvious and will in part be apparent from the specification.

The invention accordingly comprises the features of construction, combinations of elements, and arrangement of parts which will be exemplified in the construction hereinafter set forth, and the scope of the invention will be indicated in the claims.

BRIEF DESCRIPTION OF THE DRAWINGS

FIG. 14 is illustrative of comparisons of light distribution according to Examples 1 to 8 with that according to the prior art.

DESCRIPTION OF THE PREFERRED EMBODIMENTS

Figure 1:
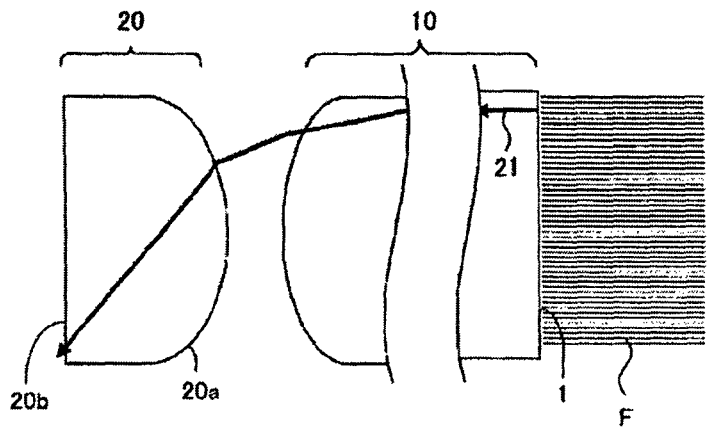
FIG. 1 is illustrative in schematic of a conventional illumination optical system: it is indicative of how the parallel light beam travels.
Figure 2:
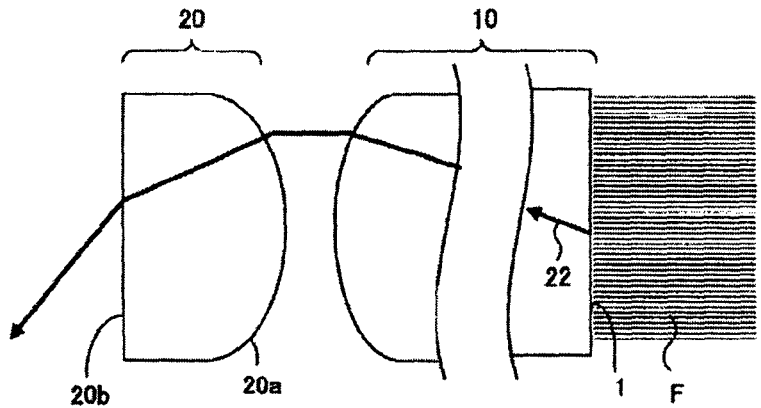
FIG. 2 is illustrative in schematic of a conventional illumination optical system: it is indicative of how the oblique light beam travels.
Figure 3:
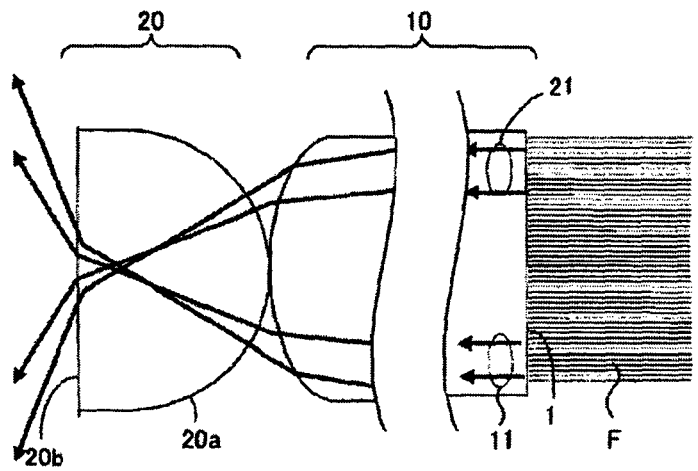
FIG. 3 is illustrative in schematic of the inventive illumination optical system: it is indicative of how the parallel light beam travels.
Figure 4:
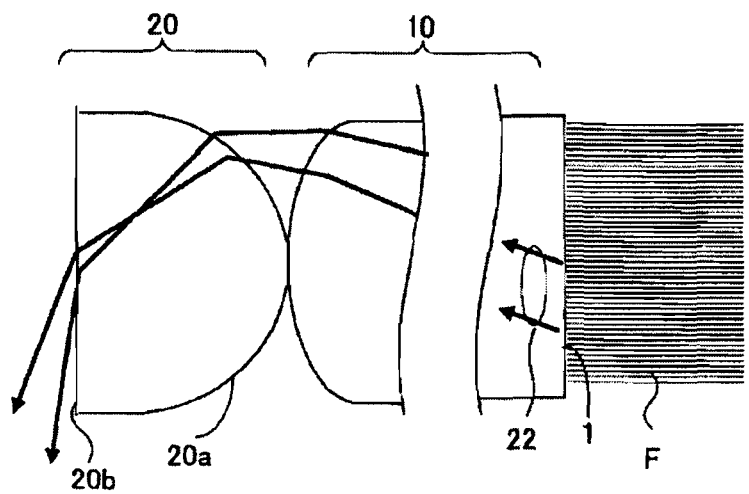
FIG. 4 is illustrative in schematic of the inventive illumination optical system: it is indicative of how the oblique light beam travels.
Figure 5:
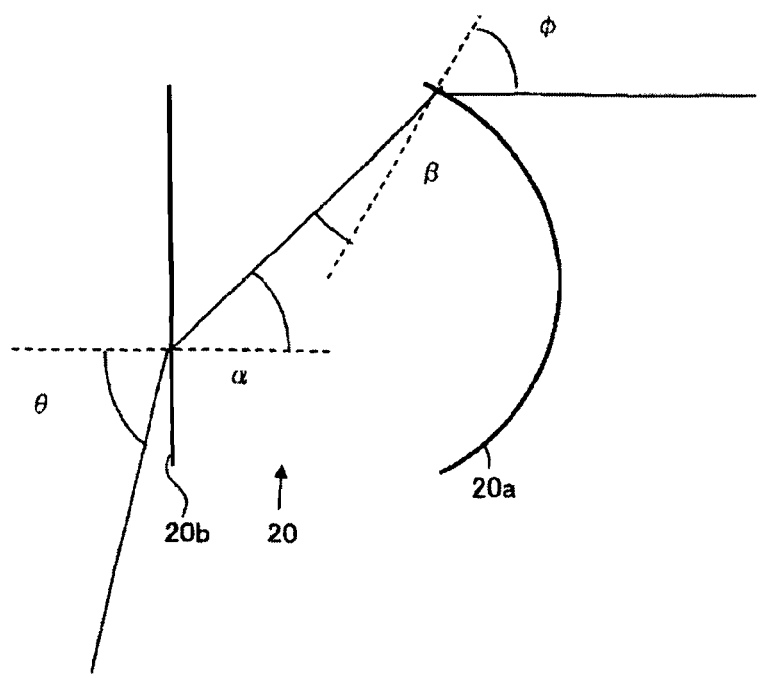
FIG. 5 is a geometrically optical view for deriving Condition (1).

Examples 1 to 8 of the inventive illumination optical system for endoscopes will now be explained with reference to FIGS. 6 to 13. In any case, from a light beam exit end 1 of a light transmission member (FIG. 3), there is a lens group 10 of positive power, followed by an optical member 20 comprising a spherical surface 20a that functions as a lens., has a radius of curvature R, and satisfies Condition (1). In some examples, there is a covering member 30 provided that has a radius of curvature having the same sign as that of the radius of curvature of the surface 20b of the optical member 20 facing the object to be illuminated or an infinite radius of curvature, thereby holding back decentration of the optical member 20. Note here that the lens located in the lens group 10 of positive power and nearest to the light beam exit end 1 may be a rod lens 11 composed of a core 11a and a cladding 11b or, alternatively, a lens from which the cladding 11b has been removed and which has a mirror surface side.

Numerical data on the lens system of each example will be given later, and they will be normalized at a focal length of 1 mm. The surface number of each optical surface, No., is counted from the side of the object to be illuminated, and the final surface is defined by the light beam exit end. The radius of curvature "r" and surface-to-surface space "d" are given in mm, and the refractive index "ne" and Abbe constant "ve" are given on an e-line basis, and in the case of the core/clad rod lens, the value of the core is given. Note here that $ve=(ne-1)/(n_{F'}-n_{C'})$ where $n_{F'}$ is the F'-line refractive index and $n_{C'}$ is the C'-line refractive index.

It is noted that optical surfaces with Surface Nos. 1, 2, 3, . . . are indicated by $r_1, r_2, r_3, \ldots$, and surface-to-surface spaces or air spaces between Surface Nos. 1 and 2, Surface Nos. 2 and 3, Surface Nos. 3 and 4, . . . are indicated by $d_1, d_2, d_3, \ldots$.

EXAMPLE 1

Figure 6:
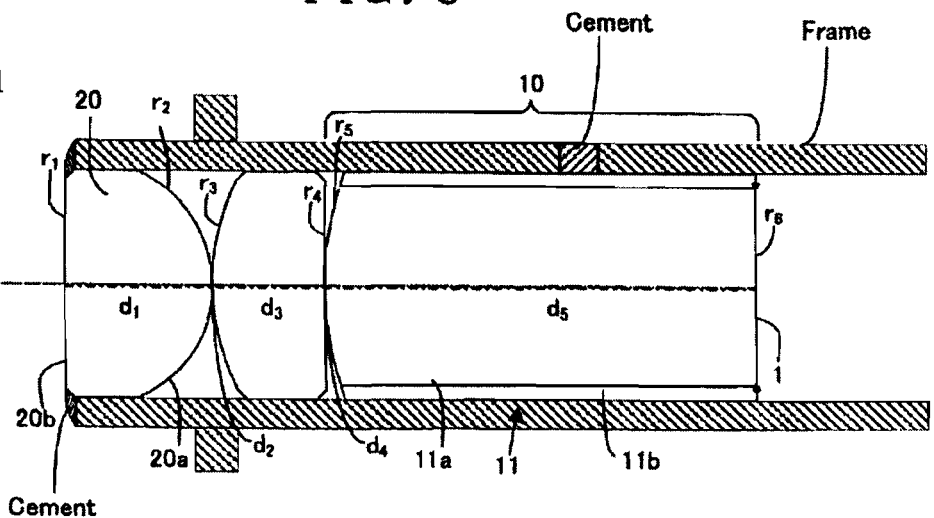
FIG. 6 is illustrative in construction of Example 1 of the inventive illumination optical system.

FIG. 6 is illustrative in section of the illumination optical system for endoscopes according to Example 1. The optical member 20 is formed of a plano-convex positive lens and the lens group 10 of positive power is made up of a convex-plano positive lens form of rod lens 11. In the table, given later, indicative of numerical data for Example 1, the second surface satisfies Condition (1), and insertion of an outer diameter of 2.86 gives $S/\pi R^2=1.58$. The third to sixth surfaces define the lens group 10 of positive power, and the sixth surface is the light beam exit end 1. The lens made up of the fifth and sixth surface located nearest to the light beam exit end is configured as a rod lens or a lens 11 having a mirror surface on the side. The refractive index and Abbe constant in the numerical data are those of the core material, and the cladding material is formed of a low refractive-index material such as soda lime glass (made by AGC and having a refractive index of 1.52). Throughout the examples, the optical surfaces may be each coated with a single layer or multilayer coating to eliminate quantity losses due to reflected light.

EXAMPLE 2

Figure 7:
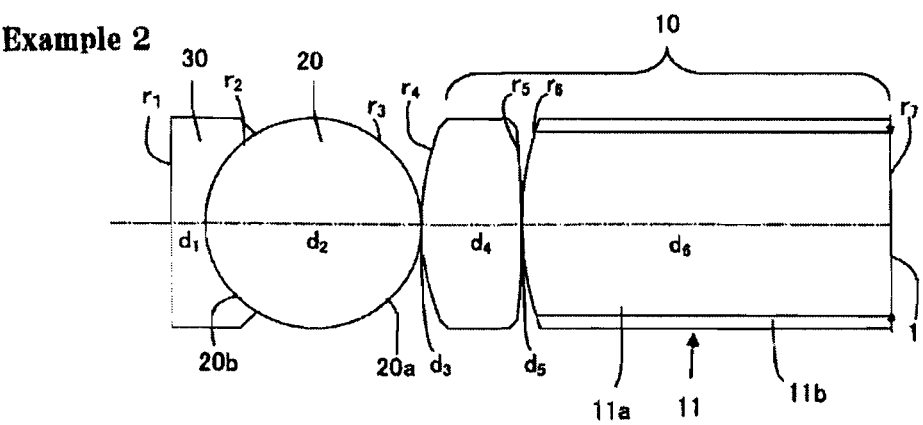
FIG. 7 is illustrative in construction of Example 2 of the inventive illumination optical system.

FIG. 7 is illustrative in section of the illumination optical system for endoscopes according to Example 2. The optical member 20 is formed of a transparent sphere, and the lens group 10 of positive power is made up of a double-convex positive lens and a convex-plano positive lens form of rod lens 11. The plano-concave negative lens form of covering member 30 is in close contact with the optical member 20. In the table, given below, indicative of numerical data on Example 2, the second and third surfaces satisfy Condition (1). The transparent sphere 20 is engaged with and fixed to the covering member 30 having the first and second surfaces, with the satisfaction of $S/\pi R^2=4$ irrespective of the outer diameter. The covering member 30 may be bonded to or in optical contact with the transparent sphere 20. Here, when the lenses are fixed in place, the covering member 30 and transparent sphere 20, each having an adhesive applied, are fixed to a frame. However, if the covering member 30 is chamfered, it is then possible to provide the outer periphery of the surface of contact of the covering member 30 and transparent sphere 20 with an escape route (groove) for an adhesive, offering an advantage that an overflow of the adhesive to the third surface is minimized. This does not always require the use of the transparent sphere: it is possible whenever the covering member 30 with a chamfer is used. The same will also go for the following examples. The fourth, fifth, sixth and seventh surfaces define the lens group 10 of positive power, and the seventh surface stands for the light beam exit end 1. The lens positioned nearest to the light beam exit end and composed of the sixth and seventh surfaces is a rod lens or a lens 11 having a mirror surface on the side.

EXAMPLE 3

Figure 8:
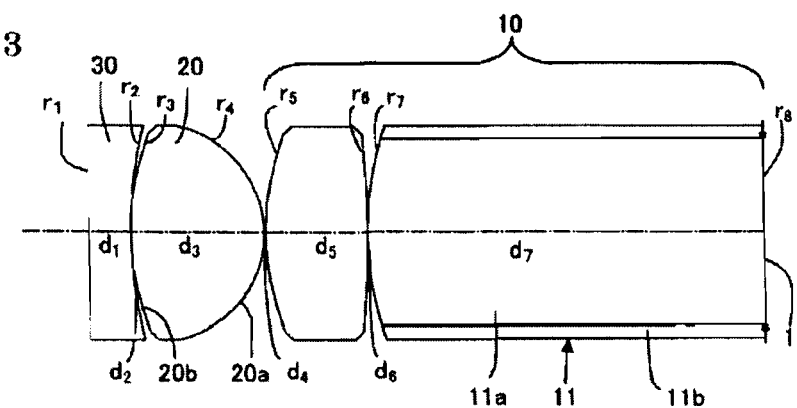
FIG. 8 is illustrative in construction of Example 3 of the inventive illumination optical system.

FIG. 8 is illustrative in section of the illumination optical system for endoscopes according to Example 3. The optical member 20 is formed of a double-convex positive lens, and the lens group 10 of positive power is made up of a double-convex positive lens and a convex-plano lens form of rod lens 11. A plano-concave negative lens form of covering member 30 is axially engaged with the optical member 20. In the table, given later, indicative of numerical data on Example 3, the fourth surface satisfies Condition (1). The outer diameter of this lens is determined by the spherical surface having the radius of curvature of the fourth surface: $S/\pi R^2 \geq 2$. The fifth, sixth, seventh and eighth surfaces define the lens group 10 of positive power, and the eighth surface stands for the light beam exit end 1. The lens positioned nearest to the light beam exit end and composed of the seventh and eighth surfaces is a rod lens or a lens 11 having a mirror surface on the side.

EXAMPLE 4

Figure 9:
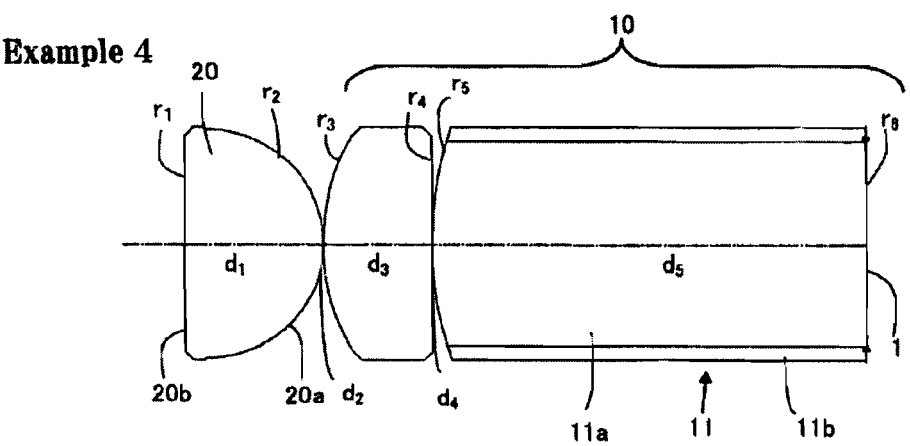
FIG. 9 is illustrative in construction of Example 4 of the inventive illumination optical system.

FIG. 9 is illustrative in section of the illumination optical system for endoscopes according to Example 4. The optical member 20 is formed of a plano-convex positive lens, and the lens group 10 of positive power is made up of a convex-plano positive lens and a convex-plano positive lens form of rod lens 11. In the table, given later, indicative of numerical data on Example 4, the second surface satisfies Condition (1). The outer diameter of this lens 20 is determined by the spherical surface having the radius of curvature of the second surface: $S/\pi R^2 \geq 2$. The third, fourth, fifth and sixth surfaces define the lens group 10 of positive power, and the sixth surface stands for the light beam exit end 1. The lens positioned nearest to the light beam exit end and composed of the fifth and sixth surfaces is a rod lens or a lens 11 having a mirror surface on the side.

EXAMPLE 5

Figure 10:
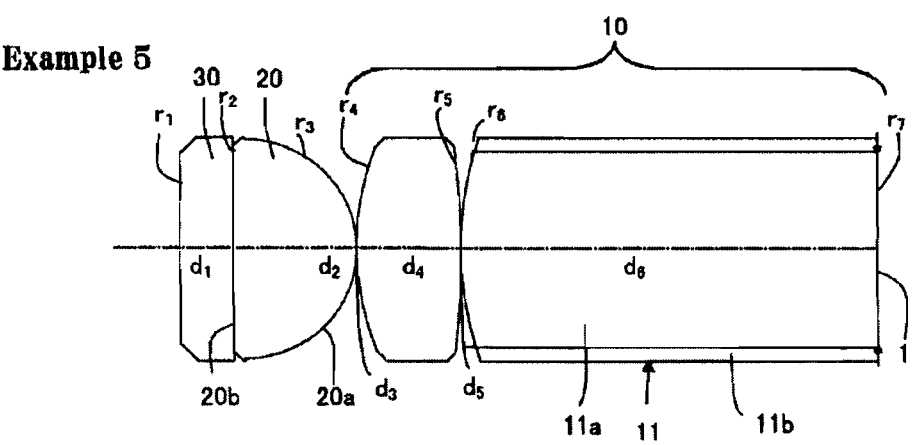
FIG. 10 is illustrative in construction of Example 5 of the inventive illumination optical system.

FIG. 10 is illustrative in section of the illumination optical system for endoscopes according to Example 5. The optical member 20 is formed of a plano-convex positive lens, and the lens group 10 of positive power is made up of a double-convex positive lens and a convex-plano positive lens form of rod lens 11. A parallel-plane plate form of covering member 30 is in close contact with the optical member 20. In the table, given later, indicative of numerical data on Example 5, a substantially transparent, hemispheric form of optical member 20 is engaged with and fixed to the covering member 30, and the third surface satisfies Condition (1). The outer diameter of this lens 20 is determined by the spherical surface having the radius of curvature of the third surface: $S/\pi R^2 \geq 2$. The fourth, fifth, sixth and seventh surfaces define the lens group 10 of positive power, and the seventh surface stands for the light beam exit end 1. The lens positioned nearest to the light beam exit end and composed of the sixth and seventh surfaces is a rod lens or a lens 11 having a mirror surface on the side.

EXAMPLE 6

Figure 11:
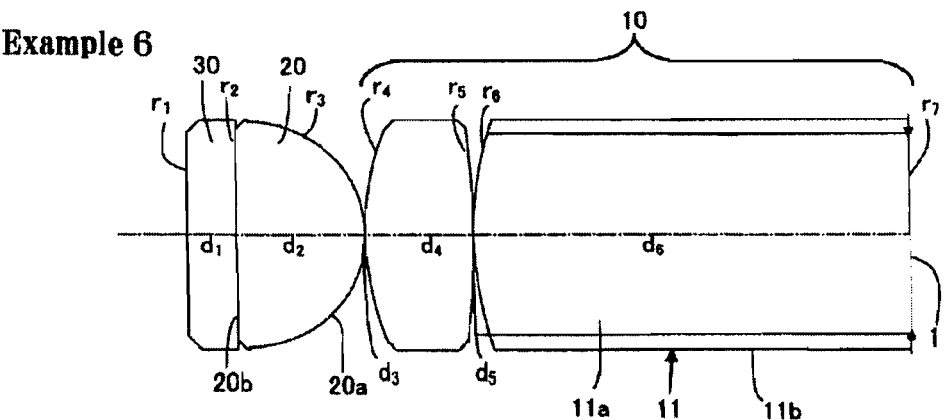
FIG. 11 is illustrative in construction of Example 6 of the inventive illumination optical system.

FIG. 11 is illustrative in section of the illumination optical system for endoscopes according to Example 6. The example here is similar in arrangement to Example 5 with the exception that the parallel-plane plate forming the covering member 30 nearest to the object to be illuminated is replaced by sapphire. This parallel-plane plate may be affixed to the frame.

EXAMPLE 7

Figure 12:
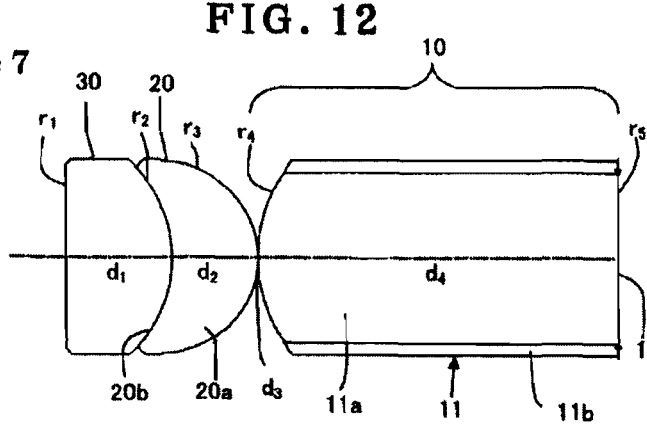
FIG. 12 is illustrative in construction of Example 7 of the inventive illumination optical system.

FIG. 12 is illustrative in section of the illumination optical system for endoscopes according to Example 7. The optical member 20 is formed of a concave-convex positive meniscus lens, and the lens group 10 of positive power is made up of a convex-plano positive lens form of rod lens 11. A plano-convex positive lens form of covering member 30 is in close contact with the optical member 20. In the table, given later, indicative of numerical data on Example 7, the covering member 30 defined by the first and second surfaces is engaged with and fixed to the covering member 20, and the third surface satisfies Condition (1). The covering member 30 and the optical member 20 may be bonded together. The outer diameter of this lens 20 is 2.54: $S/\pi R^2=1.74$. The fourth and fifth surfaces define the lens group 10 of positive power, and the fifth surface stands for the light beam exit end 1. The lens defined by the fourth and fifth surfaces and positioned nearest to the light beam exit end is a rod lens or a lens 11 having a mirror surface on the side.

EXAMPLE 8

Figure 13:
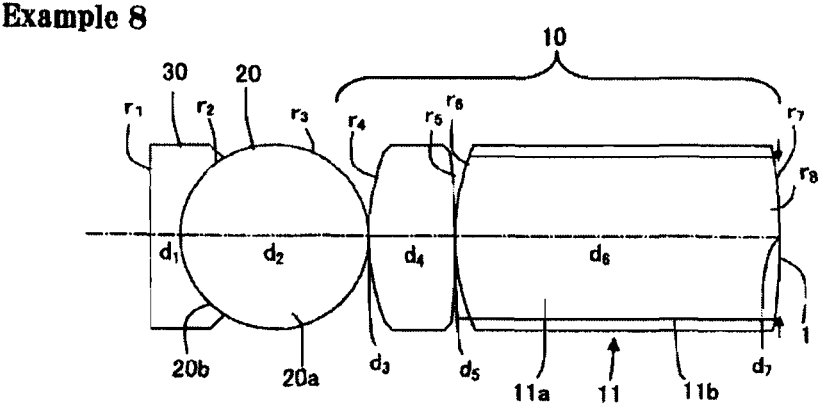
FIG. 13 is illustrative in construction of Example 8 of the inventive illumination optical system.

FIG. 13 is illustrative in section of the illumination optical system for endoscopes according to Example 8. The optical member 20 is formed of a transparent sphere, and the lens group 10 of positive power is made up of a double-convex positive lens and a double-convex positive lens form of rod lens 11. A plano-concave negative lens form of covering member 30 is in close contact with the optical member 20. In the table, given later, indicative of numerical data for Example 8, the second and third surfaces satisfy Condition (1). The covering member 30 defined by the first and second surfaces is engaged with and fixed to the transparent sphere 20, and $S/\pi R^2=4$ is satisfied irrespective of the outer diameter. The covering member 30 and transparent sphere 20 may be bonded together or in optical contact with each other. The fourth to seventh surfaces define the lens group 10 of positive power, and the eighth surface is the light beam exit end 1. A lens made up of the sixth and seventh surfaces located nearest to the light beam exit end is configured as a rod lens or a lens 11 having a mirror surface on the side.

| No | r | d | ne | ve |
|---|---|---|---|---|
| | | Example 1 | | |
| 1 | ∞ | 1.7850 | 1.88300 | 40.76 |
| 2 | −1.5720 | 0.0000 | | |
| 3 | 3.1061 | 1.3721 | 1.88300 | 40.76 |
| 4 | ∞ | 0.0000 | | |
| 5 | 4.3908 | 5.2689 | 1.80518 | 25.42 |
| 6 | ∞ | 0.0000 | | |
| | | Example 2 | | |
| 1 | ∞ | 0.4006 | 1.88300 | 40.76 |
| 2 | 1.3021 | 2.6041 | 1.77250 | 49.60 |
| 3 | −1.3021 | 0.0000 | | |
| 4 | 3.2872 | 1.2219 | 1.78800 | 47.37 |
| 5 | −12.8203 | 0.0000 | | |
| 6 | 4.0063 | 4.5071 | 1.80518 | 25.42 |
| 7 | ∞ | 0.0000 | | |
| | | Example 3 | | |

-continued

| No | r | d | ne | ve |
|---|---|---|---|---|
| 1 | ∞ | 0.4711 | 1.88300 | 40.76 |
| 2 | 5.0015 | 0.0000 | | |
| 3 | 3.0980 | 1.5181 | 1.77250 | 49.60 |
| 4 | −1.2491 | 0.0192 | | |
| 5 | 3.2536 | 1.1571 | 1.84666 | 23.78 |
| 6 | −11.9141 | 0.0000 | | |
| 7 | 3.7687 | 4.5225 | 1.80518 | 25.42 |
| 8 | ∞ | 0.0000 | | |
| Example 4 | | | | |
| 1 | ∞ | 1.6465 | 1.88300 | 40.76 |
| 2 | −1.4029 | 0.0000 | | |
| 3 | 2.6345 | 1.3172 | 1.80518 | 25.42 |
| 4 | ∞ | 0.0000 | | |
| 5 | 4.3908 | 5.2689 | 1.80518 | 25.42 |
| 6 | ∞ | 0.0000 | | |
| Example 5 | | | | |
| 1 | ∞ | 0.5900 | 1.88300 | 40.76 |
| 2 | ∞ | 1.3838 | 1.78800 | 47.37 |
| 3 | −1.2632 | 0.0000 | | |
| 4 | 3.2441 | 1.1861 | 1.80518 | 25.42 |
| 5 | −9.8747 | 0.0000 | | |
| 6 | 3.9538 | 4.7446 | 1.80518 | 25.42 |
| 7 | ∞ | 0.0000 | | |
| Example 6 | | | | |
| 1 | ∞ | 0.5300 | 1.76820 | 71.79 |
| 2 | ∞ | 1.3838 | 1.78800 | 47.37 |
| 3 | −1.2632 | 0.0000 | | |
| 4 | 3.2441 | 1.1861 | 1.80518 | 25.42 |
| 5 | −9.8747 | 0.0000 | | |
| 6 | 3.9538 | 4.7446 | 1.80518 | 25.42 |
| 7 | ∞ | 0.0000 | | |
| Example 7 | | | | |
| 1 | ∞ | 1.4356 | 1.88300 | 40.76 |
| 2 | −1.8252 | 1.1690 | 1.75500 | 52.32 |
| 3 | −1.3105 | 0.0000 | | |
| 4 | 2.0508 | 4.9220 | 1.80518 | 25.42 |
| 5 | ∞ | 0.0000 | | |
| Example 8 | | | | |
| 1 | ∞ | 0.3389 | 1.88300 | 40.76 |
| 2 | 1.1014 | 2.2028 | 1.77250 | 49.60 |
| 3 | −1.1014 | 0.0000 | | |
| 4 | 2.7806 | 1.0336 | 1.78800 | 47.37 |
| 5 | −10.8446 | 0.0000 | | |
| 6 | 2.7069 | 3.8126 | 1.80518 | 25.42 |
| 7 | −7.6131 | 0.0000 | | |
| 8 | ∞ | 0.0000 | | |

How light is distributed in Examples 1-8 is illustrated in FIG. 14, with Example 1 of Patent Publication 9 as a comparative reference.

As shown in Examples 1-8, the present invention makes it possible to use less costly lenses to set up an illumination optical system for endoscopes, which is capable of improving light distribution even at or near a half angle of view of 70°. In addition, if use is made of a lens whose outer diameter is guaranteed by a spherical surface, it is then possible to increase the precision of that outer diameter: this is effective for prevention of biased light distribution.

What we claim is:

1. An illumination optical system for endoscopes in combination with a light beam transmission means of an endoscope, said light beam transmission means of an endoscope being formed of light guide fibers that transmit light emitted from a light source, said illumination optical system for endoscopes positioned opposite a light beam exit end of the light beam transmission means of an endoscope for transmitting light emitted from the light source and characterized by comprising, as viewed from said light beam exit end, a lens group having positive power and an optical member subsequent thereto which has a spherical surface that functions as a lens, has a radius of curvature R, and satisfies the following condition:

$$1.48 \leq S/\pi R^2 \leq 4 \quad (1)$$

where
R is a radius of curvature of the spherical surface in mm, and
S is a surface area of the spherical surface, in $mm^2$.

2. The illumination optical system for endoscopes according to claim 1, characterized in that said optical member is a sphere formed of a transparent member, and the surface that functions as a lens satisfies $S/\pi R^2 = 4$.

3. The illumination optical system for endoscopes according to claim 1, characterized in that said optical member is a double-convex lens, both surfaces of which are a spherical surface having a radius of curvature R and whose centers of curvature are in alignment.

4. The illumination optical system for endoscopes according to claim 1, characterized in that said optical member is a positive lens that satisfies $2 < S/\pi R^2$ and has an outer diameter determined by a spherical surface having a radius of curvature R.

5. The illumination optical system for endoscopes according to claim 1 characterized by further comprising
a transparent covering member includes a surface that has either the same sign of radius of curvature as the surface of said optical member facing an object to be illuminated or an infinite radius of curvature, and is in at least partial contact with said optical member.

6. The illumination optical system for endoscopes according to claim 5, characterized in that said transparent covering member includes a surface that has the same radius of curvature as that of the surface of said optical member facing the object to be illuminated.

7. The illumination optical system for endoscopes according to claim 5, characterized in that said transparent covering member is affixed to a frame for stowing away an illumination lens.

8. The illumination optical system for endoscopes according to claim 1, characterized in that a lens located in said lens group of positive power and nearest to said light beam exit end is a rod lens.

9. The illumination optical system for endoscopes according to claim 8, characterized in that said rod lens is a double-convex lens.

10. An illumination optical system for endoscopes in combination with a light beam transmission means of an endoscope, said light beam transmission means of an endoscope being formed of light guide fibers that transmit light emitted from a light source, said illumination optical system for endoscopes positioned opposite a light beam exit end of the light beam transmission means of an endoscope for transmitting light emitted from the light source and characterized in that a lens group is constructed such that all lenses thereof come in contact with an adjacent lens of the lens group at their surface vertexes, and further characterized by comprising, as viewed from said light beam exit end, a lens group having positive power and an optical member subsequent to thereto which has a spherical surface that functions as a lens, has a radius of curvature R, and satisfies the following condition:

$$1.48 \leq S/\pi R^2 \leq 4 \quad (1)$$

where
R is a radius of curvature of the spherical surface in mm, and
S is a surface area of the spherical surface, in $mm^2$.

11. The illumination optical system for endoscopes according to claim 5, wherein said lens group having positive power is formed of a double-convex positive lens and a double-convex positive lens form of rod lens.

12. The illumination optical system for endoscopes according to claim 5, wherein said optical member is a plano-convex positive lens.

13. The illumination optical system for endoscopes according to claim 5, wherein a plano-concave negative lens form of covering member is in contact with the optical member.

14. The illumination optical system for endoscopes according to claim 5, wherein said optical member is a double-convex lens.

* * * * *